United States Patent [19]

Annen et al.

[11] 4,404,141
[45] Sep. 13, 1983

[54] $\Delta^{9(11)}$- AND $\Delta^{16}$-21-CHLORO-20-KETO STEROIDS OF THE PREGNANE AND D-HOMOPREGNANE SERIES, THEIR PREPARATION AND USE AS INTERMEDIATES FOR THE SYNTHESIS OF HIGHLY EFFECTIVE CORTICOIDS

[75] Inventors: Klaus Annen; Henry Laurent; Helmut Hofmeister, all of Berlin, Fed. Rep. of Germany

[73] Assignee: Schering Aktiengesellschaft, Berlin & Bergkamen, Fed. Rep. of Germany

[21] Appl. No.: 356,615

[22] Filed: Mar. 9, 1982

[30] Foreign Application Priority Data

Mar. 9, 1981 [DE] Fed. Rep. of Germany ....... 3109459

[51] Int. Cl.³ .............................................. C07J 7/00
[52] U.S. Cl. ........................... 260/397.3; 260/397.45; 260/239.55 D
[58] Field of Search ...................... 260/397.3, 397.45; /Steroids MS File

[56] References Cited

U.S. PATENT DOCUMENTS

| | | | |
|---|---|---|---|
| 3,892,857 | 7/1975 | Difazio et al. | 260/397.45 |
| 4,021,459 | 5/1977 | Green | 260/397.45 |
| 4,265,815 | 5/1981 | Varma | 260/397.45 |
| 4,277,409 | 7/1981 | Warnant et al. | 260/397.45 |

FOREIGN PATENT DOCUMENTS 2000229 7/1971 Fed. Rep. of Germany ....................... 260/397.45

Primary Examiner—Elbert L. Roberts

Attorney, Agent, or Firm—Millen & White

[57] ABSTRACT $\Delta^{16}$- and $\Delta^{17}$-21-chloro-20-keto steroids of the formula

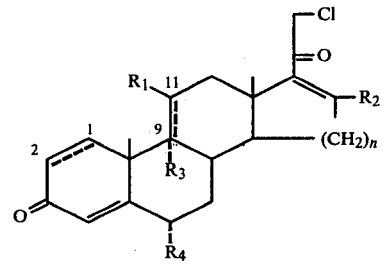

wherein n is 1 or 2, $C_1=C_2$ and $C_9=C_{11}$ represent a CC-single or CC-double bond, $R_1$ is H or OH, $R_2$ is H or $CH_3$, $R_3$ is H or F wherein, when $R_3=F$, $C_9=C_{11}$ is a CC-single bond, and $R_4$ is H, $CH_3$, or F, are valuable intermediates for preparation of highly effective, known steroids.

A process for preparing these compounds involves heating the corresponding 11β- and/or 17α- or 17aα-nitrooxy-21-mesyloxy-20-keto steroids with lithium chloride in a dipolar aprotic solvent at temperatures above room temperature.

14 Claims, No Drawings

$\Delta^{9(11)}$- AND $\Delta^{16}$-21-CHLORO-20-KETO STEROIDS OF THE PREGNANE AND D-HOMOPREGNANE SERIES, THEIR PREPARATION AND USE AS INTERMEDIATES FOR THE SYNTHESIS OF HIGHLY EFFECTIVE CORTICOIDS

BACKGROUND OF THE INVENTION

The present invention relates to new intermediates for preparing corticoidal compounds, and a process for their preparation.

It is known to prepare $\Delta^{16}$-20-keto steroids by heating the corresponding 17α-acyloxy steroids in dimethylformamide in the presence of potassium acetate [Salce et al., J. Org. Chem. 35: 1681 (1970)]. However, a prerequisite for effecting this reaction is that acyloxy residues be present in the 21-position as well as in the 17α-position. That is, for example, under the same conditions, if 17α-acetoxy-4-pregnene-6α-methyl-3,20-dione is heated, the acyloxy group in the 17α-position is not split off, whereas 17α-acetoxy-21-hydroxy-4-pregnene-3,20-dione yields, under transacylation, the 21-acetate, without, however, acquiring a $\Delta^{16}$-double bond [Solo et al., J. Org. Chem. 45: 2012 (1980)].

If the substituent in the 21-position is a chlorine atom rather than the hydroxy group, the result likewise is no $\Delta^{16}$-elimination product under these reaction conditions (Solo, loc. cit.).

It is furthermore known that, by applying the aforementioned reaction conditions to 11β,17α-dinitrooxy-21-acetoxy-20-keto steroids, the corresponding unsaturated $\Delta^{9(11),16}$-21-acetoxy-20-keto steroids are obtained (DOS [German Unexamined Laid-Open Application] 2,236,115, whose disclosures are incorporated by reference herein).

A direct procedure for the production of $\Delta^{9(11)}$- and $\Delta^{16}$-unsaturated 21-chloro steroids, however, is not known.

SUMMARY OF THE INVENTION

Accordingly, it is an object of the present invention to provide a process for the preparation of such compounds, e.g., those of formula I below.

It is another object of this invention to provide new intermediates for preparation of useful corticoids.

Upon further study of the specification and appended claims, further objects and advantages of this invention will become apparent to those skilled in the art.

These objects have been attained by providing a process comprising heating compounds of Formula II defined below with lithium chloride in a dipolar aprotic solvent to temperatures above room temperature, i.e., about 20° C.

A process of this invention for preparing $\Delta^{16}$- and $\Delta^{17}$-21-chloro-20-keto steroids, of Formula I

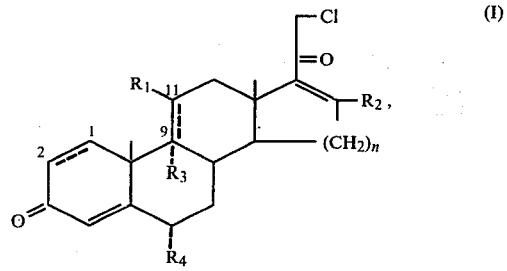

wherein n, $C_1\text{----}C_2$, $C_9\text{----}C_{11}$, $R_1$, $R_2$, $R_3$, and $R_4$ are as defined above, comprises treating the corresponding 11β- and/or 17α- or 17aα-nitrooxy-21-mesyloxy-20-keto steroid of Formula II

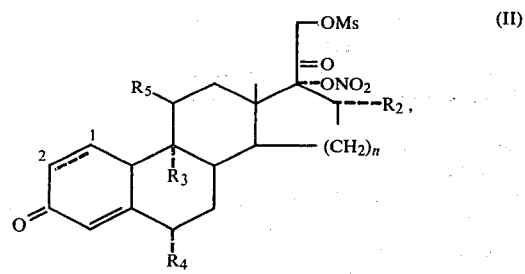

wherein
$R_2$, $R_3$, $R_4$, $C_1\text{----}C_2$ and n are as defined above,
Ms is mesyl, and
$R_5$ is hydrogen or nitrooxy,
with lithium chloride in a dipolar aprotic solvent at temperatures above room temperature, preferably at 60°–100° C.

In another aspect, these objects have been attained by providing $\Delta^{16}$- or $\Delta^{17}$-21-chloro-20-keto steroids, of Formula I

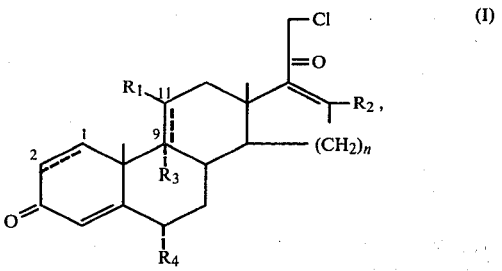

wherein
n is 1 or 2,
$C_1\text{----}C_2$ and $C_9\text{----}C_{11}$ represent a CC-single or CC-double bond,
$R_1$ is hydrogen or hydroxy,
$R_2$ is hydrogen or methyl,
$R_3$ is hydrogen or fluorine, wherein when $R_3$ is fluorine, $C_9\text{----}C_{11}$ is a CC-single bond, and
$R_4$ is hydrogen, methyl, or fluorine.

DETAILED DISCUSSION

A preferred temperature range for the process of this invention has proved to be 60° to 100° C. Reaction times are generally ½–2 hours.

Examples of suitable dipolar aprotic solvents include hexamethylphosphoric triamide, N-methylpyrrolidone, dimethylformamide, dimethyl sulfoxide, and dimethylacetamide. Especially suitable have proved to be hexamethylphosphoric triamide and N-methylpyrrolidone.

The amount of lithium chloride employed can be varied within wide limits. Suitably, 0.1–5 gram equivalents, preferably 0.5–2 gram equivalents are used, based on the number of equivalents of the steroid starting material. The amount of solvent is not critical and is conventional.

The course of the reaction according to this invention is unexpected insofar as, in addition to a substitution of the mesyloxy group on C-21 by chlorine, an elimination of the 17α-nitrate group takes place. Furthermore, the reaction of this invention proceeds by way of 21-chloro-17α-nitrate intermediates; the further reaction of these to $\Delta^{16}$-elimination products could not be foreseen, inasmuch as the corresponding 21-chloro-17α-acyloxy derivatives do not yield any $\Delta^{16}$-products under analogous conditions. Moreover, the $\Delta^{16}$-introduction via 21-chloro-17α-nitrate compounds was surprising since thus far 17α-nitrate eliminations have been described only in the presence of 21-acyloxy groups (DOS 2,236,115). Earlier attempts of the inventors of this invention to convert 21-chloro-17α-nitrate steroids with potassium acetate/dimethylformamide into the corresponding $\Delta^{16}$-elimination products have met with failure. Of course, to effect the $\Delta^{16}$-introduction, $R_5$ is nitrooxy.

All of the starting materials of formula II can be conventionally prepared, e.g., by conventional analogy to the examples given below. All the starting materials for these reactions, in turn, are also conventional or readily preparable by fully conventional methods. See also Herz et al., J. Amer. Chem. Soc., 78(1956)4812; Hofmeister et al., Chem. Ber., 107(1974)1235, whose disclosures are incorporated by reference herein.

All of the compounds of this invention are intermediates for the production of highly efficacious known corticoids. The compounds of this invention can also be used, by conventional methods, to prepare each other, and then the known corticoids can be prepared.

The known corticoid halcinonide can be prepared, for example, in a high yield from 21-chloro-4,9(11),16-pregnatriene-3,20-dione in a five-stage process. For this purpose, 21-chloro-4,9(11),16-pregnatriene-3,20-dione as the starting material is reacted by introducing the glycol group with potassium permanganate to obtain, in the first stage, 21-chloro-16α,17α-dihydroxy-4,9(11)-pregnadiene-3,20-dione. In the second stage the compound is ketalized with acetone to 21-chloro-16α,17α-isopropylidenedioxy-4,9(11)-pregnadiene-3,20-dione. In the third stage this ketal is hydroxybrominated in an aqueous solution with N-bromosuccinimide to 9α-bromo-21-chloro-11β-hydroxy-16α,17α-isopropylidenedioxy-4-pregnene-3,20-dione.

In the fourth stage the bromohydrin is converted with potassium acetate/ethanol into the 21-chloro-9β,11β-epoxy-16α,17α-isopropylidenedioxy-4-pregnene-3,20-dione.

In the fifth stage the epoxide is then finally opened up with hydrogen fluoride to the desired 21-chloro-9α-fluoro-11β-hydroxy-16α,17α-isopropylidenedioxy-4-pregnene-3,20-dione.

The use of the aforementioned intermediates of Formula I thus has the advantage over prior art methods, in particular, that with the use of comparable starting compounds, the desired final product is obtained with a substantially smaller number of reaction stages and, as a natural consequence thereof, with a higher total yield.

In general, for example, the compounds of this invention can be used to prepare the corresponding 11β-hydroxy-9α-fluoro-16α,17α-alkylidenedioxy compounds which are very useful corticoids by a series of fully conventional reactions which are analogous to those discussed above.

For example, this invention also relates to a process for preparing the 16α,17α- or 17α,17aα-alkyldienedioxy derivatives of a compound of Formula I comprising reacting the corresponding compound of claim 1 with a glycolating reagent to form the corresponding 16α,17α- or 17α,17α-dihydroxy compound, and ketalizing the latter with a ketone to form the 16α,17α- or 17α,17aα-alkylidenedioxy compund and to such a process wherein the starting compound of formula I is one in which $C_9$ $C_{11}$ is a CC-double bond and which further comprises, reacting the alkylidenedioxy compound with a hydroxybrominating reagent to form the corresponding 9α-fluoro-11β-hydroxy compound, reacting the latter with an epoxidation reagent to form the corresponding 9β,11β-epoxy compound and reacting the latter with hydrogen fluoride to prepare the corresponding 9α-fluoro-11β-hydroxy compound.

The use of the corticoids is fully conventional. Especially, they are used as anti-inflammatory agent, e.g., for the treatment of dermatosis, acute and chronic eczema etc.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

The example set forth below shows the use of this compound of Formula I as an intermediate.

At 0° C., a solution of 4.5 g of potassium permanganate in 745 ml of aqueous acetone (85% acetone + 15% water) is added dropwise within 45 minutes to a solution of 9.8 g of 21-chloro-4,9(11),16-pregnatriene-3,20-dione in 745 ml of acetone and 2.75 ml of concentrated formic acid. The product is then vacuum-filtered over sodium sulfate, the residue washed in methylene chloride, and the filtrate introduced into water. After the usual working-up operation, the mixture is concentrated to dryness under vacuum. Yield: 10.8 g of 21-chloro-16α,17α-dihydroxy-4,9(11)-pregnadiene-3,20-dione, mp 202.5°–204° C.

$[\alpha]_D^{25}$ +98°.

15.3 g of 21-chloro-16α,17α-dihydroxy-4,9(11)-pregnadiene-3,20-dione is stirred in 1,140 ml of acetone and 5 ml of 70% perchloric acid for 1 hour at room temperature. After the usual working up operation, 18.6 g of 21-chloro-16α,17α-isopropylidenedioxy-4,9(11)-pregnadiene-3,20-dione is isolated, mp 263°–266° C.

A solution of 1.0 g of 21-chloro-16α,17α-isopropylidenedioxy-4,9(11)-pregnadiene-3,20-dione in 16.9 ml of dioxane and 1.2 ml of water is combined at an internal temperature of 20° C. with 900 mg of N-bromosuccinimide in incremental portions. After adding a solution of 0.1 ml of 70% perchloric acid in 1.4 ml of water, the mixture is further agitated at room temperature for 45 minutes, neutralizsed at an internal temperature of 30

15° C. with a solution of 390 mg of sodium acetate and 250 mg of sodium sulfite in 2.5 ml of water, and after adding 15 ml of methanol, the reaction product is precipitated with water, vacuum-filtered, and the residue dried under vacuum. Yield: 0.8 g of 9α-bromo-21-chloro-11β-hydroxy-16α,17α-isopropylidenedioxy-4-pregnene-3,20-dione, mp 165° C. (decomposition).

$[\alpha]_D^{25} + 140°$.

A solution of 700 mg of 9α-bromo-21-chloro-11β-hydroxy-16α,17α-isopropylidenedioxy-4-pregnene-3,20-dione in 35 ml of ethanol is refluxed for 55 minutes with 980 mg of potassium acetate. The mixture is concentrated to half its size under vacuum and, after ice water precipitation, is worked up as usual. Yield: 615 mg of 21-chloro-9α,11β-epoxy-16α,17α-isopropylidenedioxy-4-pregnene-3,20-dione, mp 236°–238° C.

At −15° C., 3.3 g of 21-chloro-9β,11β-epoxy-16α,17α-isopropylidenedioxy-4-pregnene-3,20-dione is stirred for 1 hour in 12.5 ml of hydrogen fluoride/pyridine and worked up as usual after ice water precipitation. The crude product is purified on 300 g of silica gel with a methylene chloride-acetone gradient (0–15% acetone). Yield: 2.4 g of 21-chloro-9α-fluoro-11β-hydroxy-16α,17α-isopropylidenedioxy-4-pregnene-3,20-dione, mp 267.5°–269° C.

$[\alpha]_D^{25} + 167°$ (pyridine).

In the same way, the conventional 21-chloro-9α-fluoro-11β-hydroxy-16α,17α-isopropylidenedioxy-6α-methyl-1,4-pregnadiene-3,20-dione (U.S. Pat. No. 3,048,581, whose disclosure is incorporated by reference herein) can be advantageously produced with the use of the process of this invention.

For this purpose, the starting material is the compound of Formula I, 21-chloro-6α-methyl-1,4,9(11),16-pregnatetraene-3,20-dione, and the same, known reaction stages are executed as in case of the previously described halcinonide synthesis.

The following example is to describe this course of the synthesis:

200 mg of 21-chloro-6α-methyl-1,4,9(11),16-pregnatetraene-3,20-dione is reacted to 218 mg of 21-chloro-16α,17α-dihydroxy-6α-methyl-1,4,9(11)-pregnatriene-3,20-dione and worked up; mp 182°–186° C.

$[\alpha]_D^{25} + 2.6°$.

16.7 g of 21-chloro-16α,17α-dihydroxy-6α-methyl-1,4,9(11)-pregnatriene-3,20-dione is stirred at room temperature in 1.2 l of acetone and 5.3 ml of 70% perchloric acid for 2 hours. After precipitation into water, the mixture is worked up as usual, thus isolating 18.6 g of 21-chloro-16α,17α-isopropylidenedioxy-6α-methyl-1,4,9(11)-pregnatriene-3,20-dione, mp 231.5°–233° C.

$[\alpha]_D^{25} + 313°$.

A solution of 17.6 g of 21-chloro-16α,17α-isopropylidenedioxy-6α-methyl-1,4,9(11)-pregnatriene-3,20-dione and 16.6 g of N-bromosuccinimide in 176 ml of dioxane is combined at room temperature dropwise with 88 ml of 10% perchloric acid and stirred for 1 hour. The mixture is stirred into water which contains sodium sulfite, filtered off, and worked up as usual. Yield: 20.5 g of 9α-bromo-21-chloro-11β-hydroxy-16α,17α-isopropylidenedioxy-6α-methyl-1,4-pregnadiene-3,20-dione, mp 186°–188° C.

$[\alpha]_D^{25} + 130°$ (pyridine).

19.5 g of 9α-bromo-21-chloro-11β-hydroxy-16α,17α-isopropylidenedioxy-6α-methyl-1,4-pregnadiene-3,20-dione is refluxed in 975 ml of ethanol with 27.3 g of potassium acetate for 3 hours. The mixture is concentrated to half its size, the solution is introduced into ice water and worked up as usual, thus isolating 11.3 g of 21-chloro-9β,11β-epoxy-16α,17α-isopropylidenedioxy-6α-methyl-1,4-pregnadiene-3,20-dione, mp 191.5°–193° C.

$[\alpha]_D^{25} + 95°$.

5.0 g of 21-chloro-9β,11β-epoxy-16α,17α-isopropylidenedioxy-6α-methyl-1,4-pregnadiene-3,20-dione is added to 19 ml of a hydrofluoric acid/pyridine solution, cooled to −40° C.; the mixture is agitated for 3.5 hours at −20° C. After the mixture has been worked up, 3.8 g of 21-chloro-9α-fluoro-11β-hydroxy-16α,17α-isopropylidenedioxy-6α-methyl-1,4-pregnadiene-3,20-dione is isolated, mp 290.5°–293° C.

$[\alpha]_D^{25} 111°$.

The following examples are to explain the process of this invention.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

A suspension of 28.5 g of 21-mesyloxy-11β,17α-dinitrooxy-4-pregnene-3,20-dione in 570 ml of hexamethylphosphoric triamide is stirred at a bath temperature of 80° C. for 1.5 hours after adding 126 g of lithium chloride; the mixture is then poured on an ice water-sodium chloride solution. The residue is filtered off and washed; the crude product is chromatographed on 1.2 kg of silica gel with a hexane-ethyl acetate gradient (0–70% ethyl acetate). Yield: 13.1 g of 21-chloro-4,9(11),16-pregnatriene-3,20-dione, mp 129.5°–131° C.

$[\alpha]_D^{25} + 195°$.

Preparation of the starting material:

A suspension of 21.9 g of 11β,17α-dihydroxy-21-mesyloxy-4-pregnene-3,20-dione in 164 ml of acetic anhydride is cooled to −25° C. and combined dropwise with 105 ml of fuming nitric acid. After this dropwise addition, the mixture is further stirred for 1 hour at −15° C. and poured on an ice water-sodium chloride solution. The precipitate is filtered off, washed neutral with water, and the dissolved residue, after drying over sodium sulfate, is concentrated under vacuum. Yield of crude product: 29.2 g of 21-mesyloxy-11β,17α-dinitrooxy-4-pregnene-3,20-dione, mp 154°–156° C.

$[\alpha]_D^{25} + 73°$.

EXAMPLE 2

Analogously to Example 1, 7.2 g of 21-mesyloxy-11β,17α-dinitroxy-1,4-pregnadiene-3,20-dione is reacted to 21-chloro-1,4,9(11),16-pregnatetraene-3,20-dione and worked up. Yield: 3.6 g, mp 136.5°–138° C.

$[\alpha]_D^{25} + 149°$.

Preparation of the starting material:

Analogously to Example 1, 5.8 g of 11β,17α-dihydroxy-21-mesyloxy-1,4-pregnadiene-3,20-dione is reacted to 21-mesyloxy-11β,17β-dinitrooxy-1,4-pregnadiene-3,20-dione and worked up. Yield of crude product: 7.8 g, mp 151° C.

$[\alpha]_D^{25} + 56°$.

EXAMPLE 3

Under the conditions described in Example 1, 1.0 g of 21-mesyloxy-6α-methyl-11α,17α-dinitrooxy-1,4-pregnadiene-3,20-dione is reacted to 21-chloro-6α-methyl- 1,4,9(11),16-pregnatetraene-3,20-dione and worked up, thus isolating 486 mg of 21-chloro-6α-methyl-1,4,9(11),16-pregnatetraene-3,20-dione, mp 204°–206° C.

$[\alpha]_D^{25} + 94°$.

Preparation of the starting material:

5.75 g of 11β,17α-dihydroxy-21-mesyloxy-6α-methyl-1,4-pregnadiene-3,20-dione is reacted and worked up as described in Example 1. Crude yield: 6.3 g of 21-mesyloxy-6α-methyl-11β,17α-dinitrooxy-1,4-pregnadiene-3,20-dione, mp 164° C.

$[\alpha]_D^{25} + 48°$.

EXAMPLE 4

Under the conditions of Example 1, 10.0 g of 21-mesyloxy-17α-nitrooxy-1,4,9(11)-pregnatriene-3,20-dione is treated with lithium chloride and, after purification, 5.6 g of 21-chloro-1,4,9(11),16-pregnatetraene-3,20-dione is isolated, mp 136.5°–138° C.

$[\alpha]_D^{25} + 149°$.

Preparation of the starting material:

A solution of 10 g of 17α,21-dihydroxy-1,4,9(11)-pregnatriene-3,20-dione in 10 ml of pyridine is cooled to −20° C. and combined dropwise with 4 ml of methanesulfonic acid chloride. The mixture is then stirred for 2.5 hours at −20° C. and worked up as usual after an ice water precipitation. The crude product is purified on 1.1 kg of silica gel with a methylene chloride-acetone gradient (0–15% acetone). Yield: 9.5 g of 17α-hydroxy-21-mesyloxy-1,4,9(11)-pregnatriene-3,20-dione, mp 159°–160° C.

$[\alpha]_D^{25} + 53°$.

Analogously to Example 1, 9.0 g of 17α-hydroxy-21-mesyloxy-1,4,9(11)-pregnatriene-3,20-dione is reacted with a mixture of acetic anhydride and fuming nitric acid to obtain 10.3 g of 21-mesyloxy-17α-nitrooxy-1,4,9(11)-pregnatriene-3,20-dione, mp 165.5°–167° C.

EXAMPLE 5

Analogously to Example 1, 7.0 g of 6α-fluoro-21-mesyloxy-11β,17α-dinitrooxy-1,4-pregnadiene-3,20-dione is treated with lithium chloride, thus obtaining 4.1 g of 21-chloro-6α-fluoro-1,4,9(11),16-pregnatetraene-3,20-dione, mp 196°–200° C.

The starting material, 6α-fluoro-21-mesyloxy-11β,17α-dinitrooxy-1,4-pregnadiene-3,20-dione, was produced analogously to Examples 1 and 4 from 6α-fluoro-11β,17α,21-trihydroxy-1,4-pregnadiene-3,20-dione.

EXAMPLE 6

A solution of 1.6 g of 9α-fluoro-11β-hydroxy-21-mesyloxy-17α-nitrooxy-4-pregnene-3,20-dione in 32 ml of hexamethylphosphoric triamide is stirred with 7.0 g of lithium chloride for 0.5 hour at 80° C. bath temperature. After precipitation into ice-sodium chloride, the mixture is filtered off and worked up as usual. The crude product is chromatographed on 75 g of silica gel with a hexane-acetone gradient (0–20% acetone). Yield: 950 mg of 21-chloro-9α-fluoro-11α-hydroxy-4,16-pregnadiene-3,20-dione, mp 220°–223° C.

$[\alpha]_D^{25} + 175°$.

Production of the starting material:

Under the conditions of Example 1, 14.0 g of 9α-fluoro-11β,17α-dihydroxy-21-mesyloxy-4-pregnene-3,20-dione is reacted to 10.9 g of 9α-fluoro-11β-hydroxy-21-mesyloxy-17α-nitrooxy-4-pregnene-3,20-dione and worked up, mp 159°–161° C.

$[\alpha]_D^{25} + 45°$.

EXAMPLE 7

A suspension of 1.0 g of 21-mesyloxy-17α-nitrooxy-4-pregnene-3,20-dione in 20 ml of hexamethylphosphoric triamide is agitated at a bath temperature of 80° C. with 4.37 g of lithium chloride for 1.5 hours. After ice-sodium chloride precipitation, the mixture is filtered off and the residue worked up as usual. The crude product is chromatographed on silica gel with a methylene chloride-acetone gradient (0–12% acetone). Yield: 590 mg of 21-chloro-4,16-pregnadiene-3,20-dione, mp 167.5°–169° C.

$[\alpha]_D^{25} + 153°$.

EXAMPLE 8

Under the conditions of Example 1, 2.0 g of 9α-fluoro-11β-hydroxy-21-mesyloxy-16α-methyl-17α-nitrooxy-1,4-pregnadiene-3,20-dione is reacted to 930 mg of 21-chloro-9α-fluoro-11β-hydroxy-16-methyl-1,4,16-pregnatriene-3,20-dione and worked up, mp 250° C.

$[\alpha]_D^{25} + 144°$ (pyridine).

Preparation of the starting material:

Analogously to Example 1, 2.0 g of 9α-fluoro-11β,17α-dihydroxy-21-mesyloxy-16α-methyl-1,4-pregnadiene-3,20-dione is reacted to 1.3 g of 9α-fluoro-11β-hydroxy-21-mesyloxy-16α-methyl-17α-nitrooxy-1,4-pregnadiene-3,20-dione and worked up, mp 121.5°–123° C.

$[\alpha]_D^{25} + 13°$ (pyridine).

EXAMPLE 9

Analogously to Example 1, 1.1 g of 21-mesyloxy-17aα-nitrooxy-D-homo-4-pregnene-3,20-dione is treated with lithium chloride in hexamethylphosphoric triamide and worked up, yielding 575 mg of 21-chloro-D-homo-4,17-pregnadiene-3,20-dione, mp 132°–133° C.

Production of the starting material:

Analogously to Example 1, 3.6 g of 17α-hydroxy-21-mesyloxy-D-homo-4-pregnene-3,20-dione is reacted to 4.3 g of 21-mesyloxy-17aα-nitrooxy-D-homo-4-pregnene-3,20-dione and worked up, mp 151.5°–153° C.

EXAMPLE 10

Analogously to Example 1, a suspension of 2.85 g of 21-mesyloxy-11β,17α-dinitrooxy-4-pregnene-3,20-dione in 55 ml of N-methylpyrrolidone is agitated, after adding 12.6 g of lithium chloride, at a bath temperature of 60° C. for 2 hours and the reaction mixture is then worked up. Yield: 1.41 g of 21-chloro-4,9(11),16-pregnatriene-3,20-dione, mp 129°–132° C.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A $\Delta^{16}$-21-chloro-20-keto steroid, of the formula

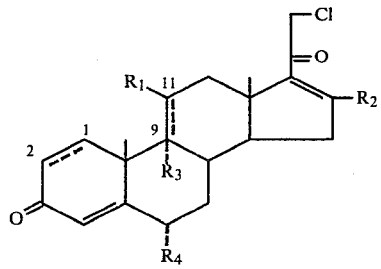

wherein $C_1\text{----}C_2$ and $C_9\text{----}C_{11}$ each independently is a CC-single or CC-double bond, $R_1$ is hydrogen or hydroxy, $R_2$ is hydrogen or methyl, $R_3$ is hydrogen or fluorine, provided that when $R_3$ is fluorine, $C_9\text{----}C_{11}$ is a CC-single bond, and $R_4$ is hydrogen, methyl, or fluorine.

2. 21-Chloro-4,9(11),16-pregnatriene-3,20-dione, a compound of claim 1.

3. 21-Chloro-1,4,9(11),16-pregnatetraene-3,20-dione, a compound of claim 1.

4. 21-Chloro-6α-methyl-1,4,9(11),16-pregnatetraene-3,20-dione, a compound of claim 1.

5. 21-Chloro-6α-fluoro-1,4,9(11),16-pregnatetraene-3,20-dione, a compound of claim 1.

6. 21-Chloro-9α-fluoro-11β-hydroxy-4,16-pregnadiene-3,20-dione, a compound of claim 1.

7. 21-Chloro-4,16-pregnadiene-3,20-dione, a compound of claim 1.

8. 21-Chloro-9α-fluoro-11β-hydroxy-16-methyl-1,4,16-pregnatriene-3,20-dione, a compound of claim 1.

9. A process for preparing a $\Delta^{9(11)}$ and/or $\Delta^{16}$-21-chloro-20-keto steroid of claim 1 of the formula

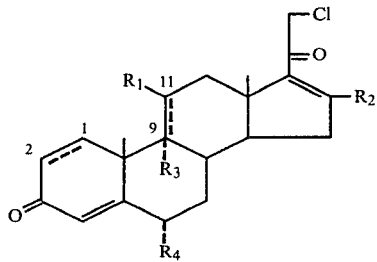

comprising treating the corresponding 11β- and/or 17aα-nitrooxy-21-mesyloxy-20-keto steroid of the formula

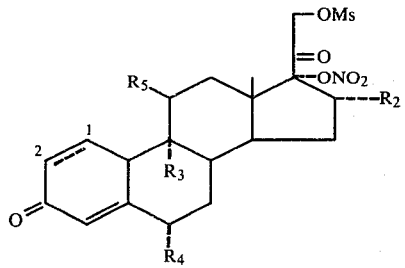

wherein $R_2$, $R_3$, $R_4$ and $C_1\text{----}C_2$ are as defined above,

Ms is mesyl, and $R_5$ is hydrogen or nitrooxy, with lithium chloride in a dipolar aprotic solvent at a temperature above room temperature.

10. A process of claim 9 wherein the treating temperature is 60°–100° C.

11. A process of claim 9, wherein the dipolar aprotic solvent is hexamethylphosphoric triamide or N-methylpyrrolidone.

12. A process for preparing the 16α,17α-alkylidenedioxy derivative of a compound of claim 1 comprising reacting the corresponding compound of claim 1 with a glycolating reagent to form the corresponding 16α,17α-dihydroxy compound, and ketalizing the latter with a ketone to form the 16α,17α-alkylidenedioxy compound.

13. A process of claim 12 wherein the starting compound of claim 1 is one in which $C_9$  $C_{11}$ is a CC-double bond and which further comprises, reacting the alkylidenedioxy compound with a hydroxybrominating reagent to form the corresponding 9α-fluoro-11β-hydroxy compound, reacting the latter with an epoxidation reagent to form the corresponding 9β,11β-compound and reacting the latter with hydrogen fluoride to prepare the corresponding 9α-fluoro-11β-hydroxy compound.

14. A $\Delta^{17}$-21-chloro-20-keto steroid of the formula

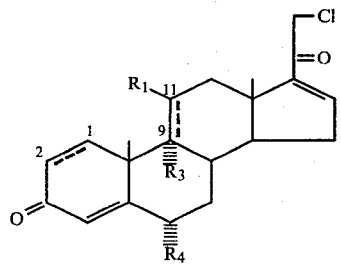

wherein $C_1\text{----}C_2$ and $C_9\text{----}C_{11}$ each independently is a CC-single or CC-double bond, $R_1$ is hydrogen or hydroxy, $R_3$ is hydrogen or fluorine, provided that when $R_3$ is fluorine, $C_9\text{----}C_{11}$ is a CC-single bond, and $R_4$ is hydrogen, methyl or fluorine.

* * * * *

UNITED STATES PATENT AND TRADEMARK OFFICE
CERTIFICATE OF CORRECTION

PATENT NO. : 4,404,141
DATED : September 13, 1983
INVENTOR(S) : KLAUS ANNEN ET AL It is certified that error appears in the above-identified patent and that said Letters Patent is hereby corrected as shown below:

Column 9, line 62: reads "17aα-nitrooxy-21-mesyloxy-20-keto steroid of the for-"
should read -- 17α-nitrooxy-21-mesyloxy-20-keto steroid of the for- --.

Signed and Sealed this

Twenty-first Day of August 1984

[SEAL]

Attest:

GERALD J. MOSSINGHOFF

Attesting Officer   Commissioner of Patents and Trademarks